United States Patent [19]

James et al.

[11] 4,322,074
[45] Mar. 30, 1982

[54] ELECTRONIC GAME SYSTEM

[75] Inventors: David F. James, Redondo Beach; Peter A. Oliphant, Van Nuys; Timothy A. Effler, Torrance, all of Calif.

[73] Assignee: Mattel, Inc., Hawthorne, Calif.

[21] Appl. No.: 113,166

[22] Filed: Jan. 18, 1980

[51] Int. Cl.³ .............................................. A63F 9/00
[52] U.S. Cl. .................................... 273/1 E; 273/85 G
[58] Field of Search ...................... 273/1 E, 85 G, 237

[56] References Cited
U.S. PATENT DOCUMENTS 4,008,893 2/1977 Yoseloff ............................ 273/85 G
4,162,792 7/1979 Chang et al. ..................... 273/85 G Primary Examiner—William H. Grieb
Attorney, Agent, or Firm—John G. Mesaros; Max Shirk; Ronald Goldman

[57] ABSTRACT

An electronic game having a display field of illuminatable segments arranged in a matrix or array of rows and columns, with a plurality of manually operable switches equal in number to the number of columns, the switches having different functions determined by the rules of one of a plurality of games playable on the electronic game. At least one segment is illuminated in a predetermined column and upon initiation of the game segments in that column are successively illuminated, one at a time. Depending on the function assigned to the switches manual operation of one of the switches causes one of three displayed results, the reversal of the direction of successive illumination, the varying of the speed of successive illumination, or the ceasing of the sequence of illumination displaying the then illuminated segment in a static condition.

25 Claims, 12 Drawing Figures

| | A | B | C | D | E | F - - - - X |
|---|---|---|---|---|---|---|
| A | | RANDOM TIME INTERVAL | LEVEL/ CATCHES | DOT 2 TIMER | DOT 1 TIMER | DOT 0 TIMER |
| B | CLOCK | SOUND DELAY 1 | | DOT 2 STAT | DOT 1 STAT | DOT 0 STAT |
| C | SCORE | SOUND DELAY 2 | | DOT 2 COL | DOT 1 COL | DOT 0 COL |
| D | MODE FLAG | SOUND FLAG | | DOT 2 ROW | DOT 1 ROW | DOT 0 ROW |

ELECTRONIC GAME SYSTEM

BACKGROUND OF THE INVENTION

The background of the invention will be discussed in two parts:

1. Field of the Invention

This invention relates to electronic amusement devices and more particularly to an electronic game having a segmented display and manually operable switches for controlling at least in part the segments so displayed.

2. Description of the Prior Art

Electronic amusement devices utilizing a display and a means for controlling one or more objects on the display have been around for many years, more recently being found in game or amusement parlors as well as the home. Some of these electronic games utilize a cathode ray tube with a joy stick or the like with the machine controlling certain objects on the screen and the joy stick controller providing manual control of another object on the screen.

In recent years, a variation of these games has appeared utilizing microprocessor technology for providing hand-held or tabletop electronic games with the displays being configured from a matrix or array of light emitting diode segments. Many of such electronic games have been configured to simulate sporting events such as football, basketball, baseball, soccer or auto race games. In all of these type games, the microprocessor controls illumination of predetermined patterns of segments which may change during play of the game. The microprocessor illuminates a player controlled segment, the position of which is determined by inputs to the microprocessor by the operator depressing one or more switches or by multiple depressions of a given switch.

One such electronic game is shown and described in U.S. Pat. No. 4,162,792 entitled "Obstacle Game" issued July 31, 1979 to Chang, et al and assigned to the Assignee of the instant invention. In that patent, a football type game and a game simulating an auto race are shown, the machine or microprocessor controlling a plurality of obstacles or indicia with the operator having control of one indicium, the position of which may be varied by manipulation of control switches.

In other of such electronic games, the display is a numeric display for displaying a number or a series of numbers with the switches for controlling the display being numeric switches, much in the manner of a hand-held calculator. Some of such games, such as a game sold under the trademark "Speak & Spell" by Texas Instruments include a display for displaying words and letters with a keyboard for entering the words and letters. Some of the numeric display calculator type games and the word display games provide multiple game modes selectable by the operator.

The electronic games available may be divided into those requiring intellectual skills (word games and number games) or those requiring manual dexterity, that is operation of a switch or key for coinciding with or avoiding the position of a segment illuminated on the display.

It is an object of the present invention to provide a new and improved electronic game system.

It is another object of the present invention to provide a new and improved electronic game having illuminatable segments selectively energized in predetermined patterns with the visual effect of the so-illuminated segment being controlled in part by timely depression of one or more switches provided.

SUMMARY OF THE INVENTION

The foregoing and other objects of the invention are accomplished by providing an electronic game system having display means including a playing field display and a numeric score indicating display. The playing field display is arranged in an array or matrix of columns and rows of illuminatable areas or segments. A plurality of manually operable switches is provided, the number of such switches corresponding to the number of columns with each switch being physically arranged in alignment with a column. The embodiment illustrated includes an array of three columns of nine rows of light emitting diode segments viewable through a display surface such as a diffuser to provide the appearance of "dots" or round illuminated objects or indicia. The normal orientation of the game for use is with the columns in a vertical alignment with the three switches being below the playing field display. A fourth switch is provided for energizing the electronic components which include a microprocessor. As part of the logic, game select means are provided, the game select being initiated upon application of power or upon completion of a game for providing a display indicative of the game select mode. In the game select mode, one of the three switches may be actuated to select one of three games. Upon selection of the games, the function associated with each of the switches is assigned in accordance with the game selected. Upon selecting a game, at least one segment in a predetermined column is illuminated and means are provided for successively illuminating in sequence, one at a time, the segments in the predetermined column, with means internal to the game monitoring the row of the then illuminated segment. Depending upon the game selected, actuation of a predetermined one of the switches in timed relation with a given output of the monitoring means interrupts the sequence of illumination to either stop the sequence and display the then illuminated segment, reverse the direction of the sequence, or vary the speed of the successive illumination sequence.

One of the so-selected games simulates juggling with segments being illuminated in each column commencing with the lowermost row and being successively illuminated upwardly and then downwardly to simulate gravity. Actuation of the switch in a given column in timed relation with the energization of a segment in a predetermined number of rows less than the total number of rows reverses the direction of the sequence to simulate throwing the ball up into the air. The numeric display during the play shows the number of seconds left counting down as time goes on and when time runs out displays the score which is the number of successful switch depressions.

A second game simulates a coin dropping with the segments in a given column being successively illuminated in sequence to simulate the motion of gravity with actuation of a switch at or prior to the lowermost row being illuminated being the object of the game. Depending on the success of the operator, the level of difficulty increases. The scoring is proportional to the level of complexity and the row number occupied by the illuminated segment at the time of successful actuation of the switch, this score being displayed on the numeric display.

A third game simulates a man in space (one illuminated segment attempting to dock with a spaceship (defined by a pattern of four illuminated segments). The spaceship pattern moves in sequence down the display, wrapping around at the bottom to the top under control of the processor with the three buttons being used to vary the speed of the "man" and to stop him in proper relation to the spaceship. Scoring is determined by the number of successful attempts or rounds, each round having a given amount of time; the time, the score and number of successful rounds being indicated on the numeric display.

Other objects, features and advantages of the invention will become apparent from a reading of the specification when taken in conjunction with the drawings in which like reference numerals refer to like elements in the several views.

DESCRIPTION OF THE PREFERRED EMBODIMENT

Figure 1:
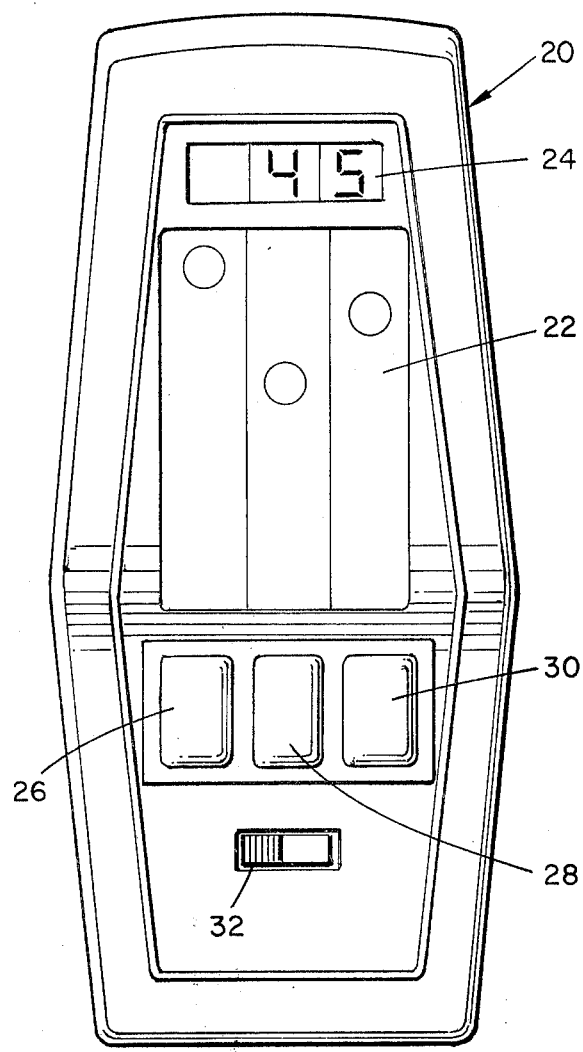
FIG. 1 is a front view of the control and display console of an electronic game according to the invention.

Referring now to the drawings, and particularly to FIG. 1 there is shown an electronic game 20 having a housing configured for providing a display portion including a playing field display 22 and a timing or scoring display 24. The scoring display 24 may be for example a conventional three digit numeric display of light emitting diodes, liquid crystal or the like.

Figure 2:
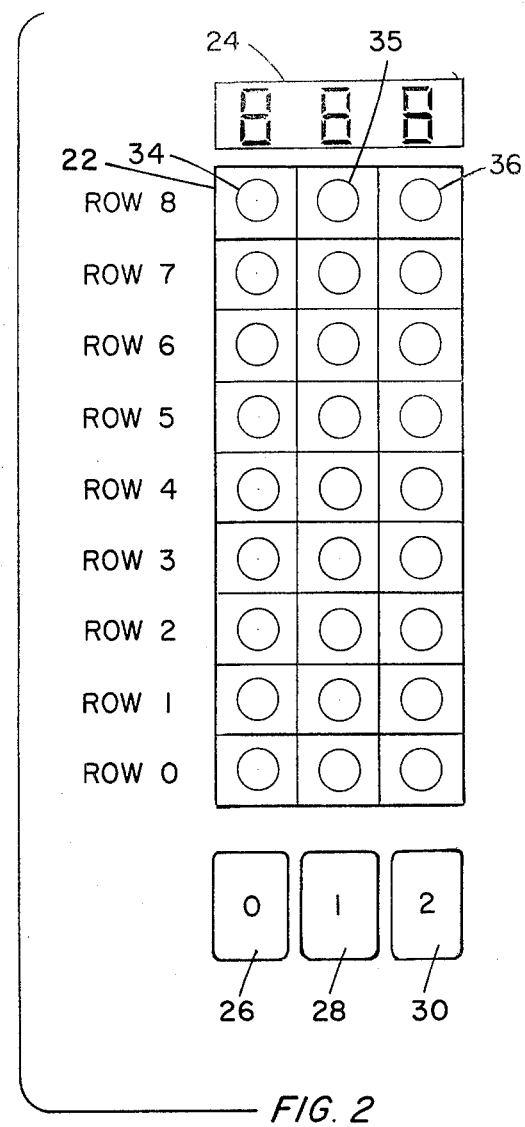
FIG. 2 is a diagramatic layout of the displays and switches with labels for row and column identification.

Referring also to FIG. 2, the playing field display 22 is a matrix or array of illuminatable segments which may be for example light emitting diode segments beneath a generally transparent cover which may be a diffuser for altering the configuration of the illuminated segments to give the visual impression of round dots. A display subassembly particularly suitable for use in the game 20 is more fully shown and described in a patent application filed concurrently herewith entitled "Electronic Games Having Light Guide Array Display" by David S. James and Elton Lynn Johnson, and assigned to Mattel, Inc., the assignee of the instant application, such application being filed Jan. 21, 1980 with Ser. No. 113,939, now U.S. Pat. No. 4,306,716, issued Dec. 22, 1981. In the embodiment illustrated, the matrix is in the form of an X-Y coordinate matrix of rows and columns, there being three columns of nine rows of aligned segments or display locations. Immediately beneath the columns there are positioned switches 26, 28 and 30, each of the switches being in vertical alignment with a column thereabove and in horizontal relation to each other. While the physical positioning of the switches 26, 28 and 30 is not a system constraint, for the games to be hereinafter described, the physical positioning is a matter of convenience and provides spatial orientation for the operator between a particular switch and an indicium or "dot" to be acted upon in the column thereabove depending on the particular game selection. A fourth switch 32 is the "on-off" switch and may be conveniently positioned anywhere on the game 20, the purpose of switch 32 being to electrically connect the battery (not shown) within the game 20 to the electronics therein.

Referring now to FIG. 2, there is diagrammatically illustrated the playing field display 22 and the control switches 26, 28 and 30. Adjacent the playing field display 22, there are designations for identifying a horizontal arrangement of illuminatable segments, the uppermost row having the segments identified by reference numerals 34–36, which in the left column is identified as row "8". For ease of description, the playing field display 22 has been divided in FIG. 2 (and FIGS. 3–5) into a grid with the center of each grid having a circle therein for illustrating the viewable indicia or "dot" locations available for selective energization for providing the illumination. For example, the segments identified by reference numerals 34–36 depict physical locations of illuminatable segments, whether or not illuminated. It is to be understood that the term "illuminatable segments" as used herein may include light emitting diode segments, liquid crystal display segments or any other portion of a display means which may be selectively energized at a defined physical location.

For ease of description, the horizontal rows of three segments each are labeled from bottom to top rows "0" through "8" with the columns being labeled by numerals within the rectangular depictions of the switches 26, 28 and 30, these being from left to right columns "0", "1" and "2". During the discussion hereinafter, for convenience, given locations of a particular segment on the matrix or grid of the playing field display 22 will be referred to by row and column number.

As will hereinafter be described, the switches 26, 28 and 30 have different assignments determined by the one of four modes in which the electronics are set at a given point in time. For example, upon initial actuation of the switch 32 to the "on" position, actuation of one of the switches 26, 28 or 30 will determine the particular game to be displayed. Once the game has been selected, at least one segment will be illuminated in a predetermined row of a predetermined column. Upon start of the game adjacent segments in the same column are successively illuminated, one at a time, in sequence until actuation of a control switch alters the display depending on game rules. The direction of successive illumination is ordinarily from one end of the column to the other, for example from a higher numbered row toward a lower numbered row. During this movement, the row numbers are monitored by continually updating a register for that column and if a defined relation exists between the time of actuation of the control switch and the row count information, the resulting display will be one of (a) a "reversal" of the direction of travel of the "dot" or (b) a "freezing" or stopping the display with that particular dot illuminated. In one of the games, two of the control switches are utilized to vary the speed of successive illumination of an operator-controlled dot with the third switch, upon actuation stopping the dot. When the term "dot" is used hereafter, it will refer to a segment which is illuminated, or a viewable game object.

Figure 3:
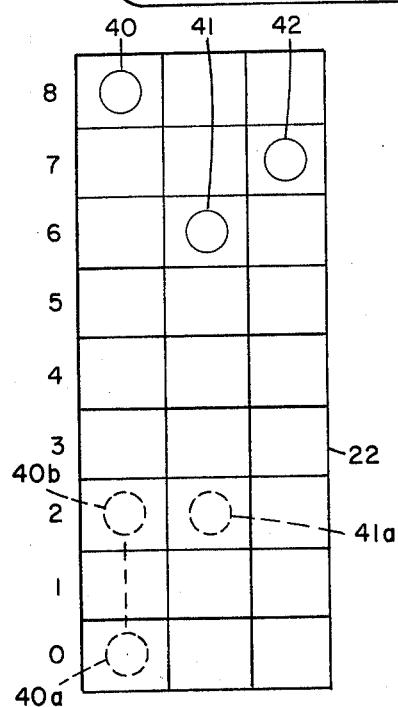
FIG. 3 is a diagramatic view of the playing field display and switches similar to FIG. 2 depicting an illuminated segment pattern for one of the games.
Figure 4:
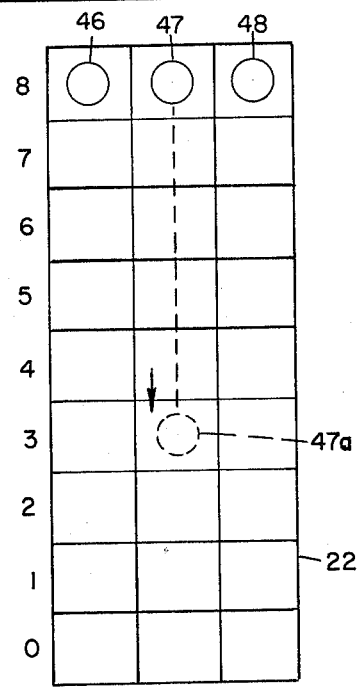
FIG. 4 is a diagramatic view of the playing field display and switches similar to FIG. 2 depicting an illuminated segment pattern for a second of the games.
Figure 5:
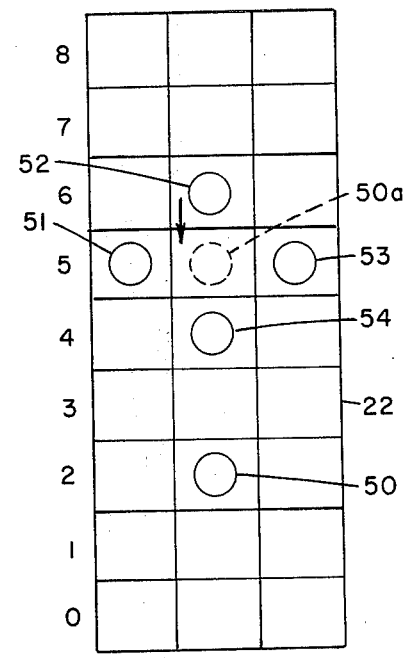
FIG. 5 is a diagramatic view of the playing field display and switches similar to FIG. 2 depicting an illuminated segment pattern for the third one of the games.

FIGS. 3 through 5 are diagramatic depictions similar to FIG. 2 showing dots on the grid of the playing field display 22, these dots corresponding to segments which may be illuminated during play of the game. Adjacent to certain of the dots, there are arrows indicating a "direction of travel", it being understood that the arrow indicates the direction of successive illumination of adjacent segments in sequence and not the moving of the dots per se. The three games, for purpose of description, will be described as a "juggling" game, a "coin drop" game, and a "spaceship docking" game.

The juggling game is depicted diagramatically in FIG. 3, the coin drop game being diagramatically illustrated in FIG. 4, and the spaceship docking game being diagramatically illustrated in FIG. 5. All three diagrams include the control switches 26, 28 and 30 in vertical alignment with the individual columns of the playing field display 22. For ease of discussion, each of the dots will be given a reference numeral different from those previously used.

Initially, with reference to FIG. 3, the juggling game is configured to simulate three balls represented as indicia by the three dots 40-42, the balls moving upwardly on the playing field display 22 with decreasing acceleration to simulate the motion of gravity with the downward travel of the balls likewise simulating the influence of gravity, that is when directed upwardly the visual appearance of the moving dots is one of increasing acceleration and then deceleration until at the top of the trajectory the direction is reversed again simulated the downward effect of gravity.

During play of this game, the electronics monitors the row location occupied by the then illuminated segment and only when any of the dots 40-42 are moving downwardly or "at rest" and in one of the predetermined rows, will the control keys 26, 28 and 30 be effective. Of the nine rows available, rows "0", "1" and "2" are in the predetermined number of rows. Briefly, by way of example, if the dot 41 in the second column is in the dotted line position designated 41a and moving downwardly, depression of the control key 28 in a timely fashion will produce a signal to the microprocessor indicating a reversal of the direction of successive illumination of the LED's 35 (see FIG. 2) in column "1", thus simulating a redirection of the dot 41 upwardly. Effectively this would simulate a successful catch of a ball to be juggled and redirected upwardly.

The row monitoring by the electronics provides one of two conditions if the ball or dot is in row "0", this position being indicated for example by the dotted representation designated 40a in the left most column "0" at row "0". In this position, the ball or dot can be "at rest" or "bouncing". The control keys 26, 28 and 30 are only effective or active if one of the dots 40-42 is moving downwardly and in rows "2", "1", or "0", and the control switches are likewise active when a dot is at rest in row "0". A bouncing condition is visually observed (for example by reference to column "0") when the dot 40 reaches row "0" as shown in dotted lines with reference numeral 40a without a successful depression of control switch 26, in which event the dot travels up to row "2" as indicated in dotted lines with reference numeral 40b then back down to the position 40a, this being defined as bouncing. If the illuminated dot is in row "0", has just arrived there and the control switch 26 is instantaneously depressed, the visual impact will be one of a successful catch with the successive illumination of the segments being directed upwardly toward the uppermost row of that column. On the other hand, after cessation of a bouncing condition, an "at rest" condition will exist, this being depicted by the reference numeral 40a adjacent the dotted line depiction of the dot in row "0" which will occur a short period of time after the dot has commenced bouncing. After this lapse of time, the control switch 26 again becomes effective permitting the "lost ball" to be directed upwardly by depression of switch 26.

During play of the juggling game one segment in row "0" in each of the three columns will be initially energized with the initial direction of travel of the dots 40-42 upwardly after depression of a control switch 26, 28 or 30 by the operator. The dots 40-42 will initially travel to row "8" and back toward row "0" unless appropriate action is taken by the operator in depressing one of the control switches 26, 28 and 30. Upon initialization of the game, the three digit display 24 (see FIG. 1) will display the initial time allowed for play of the game and will decrement downwardly at generally regular intervals until the time is exhausted. For example, if the game period is defined as 45 seconds, the initial display on the display 24 will be "45" to indicate the time, which will then count down to zero, at which time the control switches 26, 28 and 30 will become inactive, a sound will be emitted and the display will be frozen for a specified time duration, such as three seconds, after which the game 20 will automatically go into a game select mode. Other variables in conjunction with the juggling game will be discussed hereinafter.

Referring now to FIG. 4, the coin drop game will be described briefly. The game is structured to provide three levels of increasing skill after successful completion of each level, successful completion of a particular level being defined as three consecutive successful catches. A catch is defined as follows: Upon start of the game at least one segment will be illuminated in a particular column to provide a visual indication such as dot 46 in column "0". The dot 46 will appear in the uppermost row "8" and, after a random time interval, will then "drop", that is the segments in column "0" will be successively illuminated to give the visual appearance of a dropping coin. If not control is effected, that is if control switch 26 is not depressed in a timely fashion, the segments in column "0" will go blank thus simulating a coin being missed. On the other hand, if the control switch 26 is depressed while the illuminated segment or dot 46 is occupying rows "0" through "8", a successful catch will be registered with the ultimate scoring being determined by the row number occupied by the illuminated segment at the time of depression of the control switch 36. Upon a successful catch, the dot 46 will freeze or stop in that row for a moment prior to the next coin drop. That is, the segment being illuminated at the time of depression of control switch 26 will remain illuminated. During play of the coin drop game, the row count information is monitored for providing the necessary signals for scoring purposes.

Levels of complexity are defined in accordance with the rules of the game in the following manner. Immediately after commencement of the coin drop game a dot 46 will appear in the leftmost column "0" in row "8" as depicted in FIG. 4. The remainder of the display 22 will be blank, that is the dots 47 and 48 will not appear and only one segment will be illuminated. This is the first level of complexity. The indicium or dot 46 will travel downwardly in its column on the display screen 22 increasing in speed to simulate the force of gravity. Three successful catches consecutively will provide a signal or "flag" to increment the electronics to the second level of complexity. At the second level, dots will appear in two locations, these being depicted as dots 46 and 47 in columns "0" and "1" controlled by control switches 26 and 28. Only one of the dots 46 and 47 will move on the display screen 22, the particular dot selected being a pseudo-random selection. The operator is then required to manipuate either control switch 26 or control switch 28 to catch the coin before the display of segments in that column goes blank. Again, three successful catches consecutively advances the game 20 to the next level of complexity.

At the third level, three dots 46, 47 and 48 appear in the uppermost row "8" as shown in FIG. 4, but only one of the three dots will drop. At this level, the operator must visually discern which dot is moving and depress the control switch 26, 28 or 30 assigned to that particular column in which movement occurs. For example, the dot 47 may be dropping downwardly as indicated by the arrow adjacent to dotted line representation 47a at the time of depression of control switch 28, thus signifying to the microprocessor row "3" for scoring purposes.

The duration of the coin drop game is determined by a predetermined number of "rounds", a round being defined as a miss, or a catch, or pressing a wrong control switch, or pressing the right control switch before the coin drops. A miss occurs at level one, for example, when the dot 46 (see FIG. 4) has traveled down column "0" and the segment in row "0" is no longer illuminated prior to actuation of control switch 26. A catch is defined, again with respect to the same example, with coincidence of a signal from control switch 26 with the row count information being greater than or equal to zero but less than eight. The term row count is used to describe the monitoring activity of the electronics of the game 20 to identify the location of the then-illuminated segment, and for success, or a catch, the then-illuminated segment must be in one of the positions between row "0" and row "7".

Since, at the first level, the only control switch which can affect column "0" is switch 26, if either of switches 28 or 30 are depressed, this constitutes a wrong switch and starts another round. A round likewise is counted if the right switch is depressed when the row count information indicates row "8" as the then-illuminated segment. For example, the game may have 25 rounds with an occurrence of any one of the four above-enumerated events decrementing the display to indicate the number of remaining rounds.

Another aspect of the coil drop game is penalizing the player or operator any time he has a miss. For a miss the level drops one level unless the player is already at the first level at which time the player must successfully complete that level to again build up to the higher levels. Scoring is based on the number of successful catches with the score for each successful catch being proportional to the product of the level of complexity and the row number or row count for that catch. A running count is kept within the electronics to provide the sum total of the score after conclusion of all rounds, at which time a buzzer is sounded and the scoring display 24 displays this total. After a predetermined duration of time, the game then again enters the game select mode. The so-displayed score will remain until another game is selected.

Referring now to FIG. 5, the third game is diagramatically illustrated, this being the spaceship docking game. Upon initialization, a predetermined pattern of dots will appear on the playing field display 22, those being shown as a dot 50 in column "1" at row "3" and a "spaceship", the spaceship being simulated by four dots 51-54 arranged in a horizontal diamond-shaped configuration. That is, dots 51 and 53 both appear in row "5" at columns "0" and "2" respectively. Dots 52 and 54 are arranged in the center column "1" in vertical alignment in rows "6" and "4". The arrow adjacent thereto indicates downward movement of the pattern of dots 51-54 toward the dot 50 which simulates a man in space. The spaceship and man, upon initialization of this game may appear at any convenient location on the playing field 22 and the direction of travel of the spaceship can be up the screen or down the screen, this being a matter of choice. In the embodiment illustrated, the spaceship (the pattern of dots 51-54) travels down the screen and the control switches 26, 28 and 30 are assigned functions for controlling the dot 50. For example, the leftmost control switch 26 can be assigned the function of speeding the man or dot 50 up, the control switch 30 can be assigned the function of slowing the man or dot 50 down and the center control switch 28 is assigned the function of attempting docking, that is, placing the dot 50 in the center of the ship as indicated by the dotted line 50a at row "5", column "1".

After selection of the spaceship game, the display 22 will display the spaceship defined by dots 51-54 at a predetermined location which may be, for example, the spaceship pattern of dots 51-54 moved to the lowermost three rows as a group. This will place the spaceship at the lowermost position of the display screen 22. The man depicted by the dot 50 will always be positioned in the center column, that is column "1" and may be initially, for example, at row "8". The spaceship pattern of dots 51-54 will then commence movement downwardly, that is there will be sequential successive illumination of each segment of the dispaly 22 starting with the initially illuminated segments. A timer is started upon initial movement of the spaceship, this initial movement being started by depression of the control switch 30, although any of the switches may be assigned this function. The man dot 50 is then moved by the operator depressing switch 26 with successive depressions speeding up the movement of the dot 50 with switch 30 being used to slow down this movement.

In accordance with the rules of the game, the player is alloted a predetermined number of rounds (e.g. nine or ten rounds) with each round being defined as the passage of a predetermined duration of time (e.g. 20 seconds) during which time the player attempts to effect a successful docking, a successful docking being defined as the depression of the center control switch 28 with the man or dot 50 moving in synchronism with the spaceship or pattern of dots 51–54, and the man or dot 50 occupying the center of the spaceship (as indicated in the dotted line 50a of FIG. 5). If the player is unsuccessful in a given round the game terminates and the player does not advance to the next round.

As the number of successful rounds increases, the level of complexity increases. The level of complexity can be visually observed by the speed of movement of the pattern of dots 51–54 down the display 22. The visual depiction of the spaceship will appear to "wrap around" the display 22, that is the pattern of dots 51–54 will move downwardly as a unit until dots 51 and 53 are occupying row "0" at which time the dot 54 will appear in the center column row "8". In the next increment of time, the dots 51 and 53 will disappear from row "0" and appear in row "8" with dot 54 dropping down to row "7". In the next increment of time the pattern of dots 51–54 will appear in a complete pattern adjacent the uppermost portion of the display 22.

During each round of 20 seconds the spaceship will move at a constant rate, but the rate of speed will increase for each successive round. As the pattern of dots 51–54 advances along the display 22, the player manipulates the speed of the man or dot 50 to "track" the spaceship, speeding the dot 50 up or slowing it down to keep it moving until it is in the center of the spaceship at which time depression of the center control switch 28 will stop the display at which time the dot 50 will be illuminated even if it superimposes part of the spaceship, that is if the dot 50 occupies the same row as one of the dots 52 and 54 in the same column, but the overlapping dots will be brighter. If a successful docking is effected the display again stops or freezes but with the dot 50 inside the spaceship pattern of dots 51–54 (as indicated at 50a) and all of the dots are displayed. The elapsed time for a successful docking is then displayed on the numeric display 24. After a certain timed interval, such as three seconds, the display is then reset for the next round.

During a given round the numeric display 24 has two functions, these being to indicate the level the player is on and as a decrementing clock or timer to indicate to the player how much time is left in the round. During play of the game, the row count information is used, in part, to ascertain if the man or dot 50 is in horizontal alignment with the outer dots 51 and 53 of the spaceship pattern of dots, that is dots 50, 51 and 53 having the same row count.

If a successful docking is not accomplished within the time period alloted for any round, the game ends, the score is displayed and after a predetermined timed duration the game 22 goes into game select mode. Thus, a player will not advance to the next round unless all previous rounds have had successful dockings. The scoring is a function of the number of successful dockings and the time remaining in the last successful round. At the end of the game the numeric display 24 will display the score which will remain until another game is selected.

The foregoing descriptions with respect to FIGS. 3, 4 and 5 are brief descriptions of the operation of the three games playable with the game 20 and will be elaborated upon with respect to the system diagrams now to be described.

Figures 6, 12:
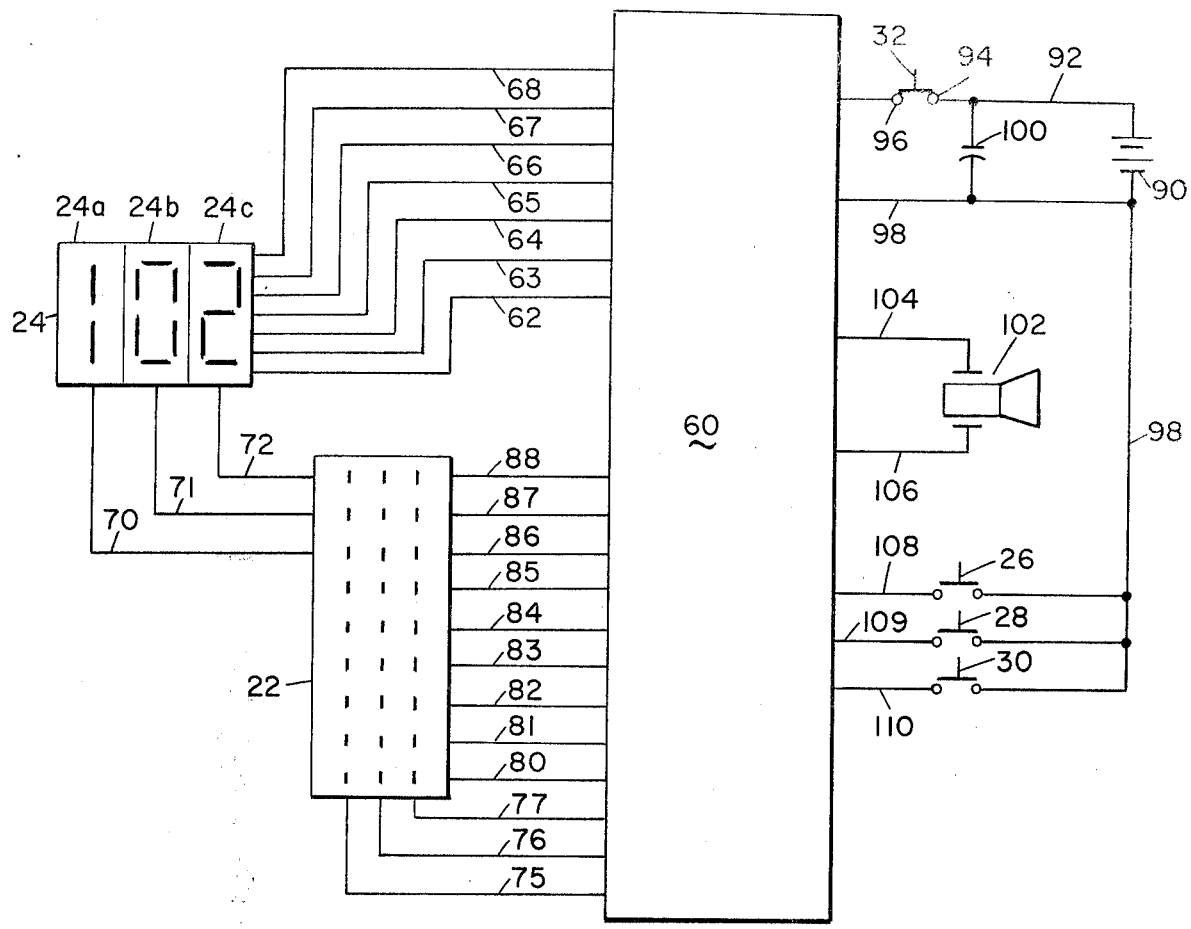
FIG. 6 is a system block diagram depicting the display elements and switches connected to a microprocessor.
FIG. 12 is a diagram of memory locations in the read/write memory of FIG. 7.

Referring now to FIG. 6, there is shown a system block diagram of the electronic portion of the game 22 which includes a microprocessor 60 which may be, for example, a microprocessor of the type sold by Rockwell International Corporation under the designation B6000 Series. A more detailed explanation of the microprocessor 60 will be discussed hereinafter with respect to FIG. 7. The microprocessor 60 is electrically connected to the three digit scoring display 24 and to the 3×9 matrix playing field display 22 by "strobe" and "segment" outputs, and conventionally, upon coincidence of a particular strobe signal and segment signal, the light emitting diode segment at that intersection will be energized and thus illuminated.

The scoring display 24 is the type of display referred to as a "segmented" display, that is it includes digit locations identified as 24a, 24b and 24c with each digit location including seven segments arranged upon illumination to provide any of the numerals zero through nine. Such segmented displays generally require seven segment inputs, these inputs being input leads 62–68 from the first set of segment outputs from the microprocessor 60. Each of the digit locations 24a–24c requires a strobe input, these strobe inputs being received over leads 70–72 respectively.

For the playing field display 22, the segment select is provided from leads 75–77 from a second segment output of the microprocessor 60, these leads being connected to the columns, there being three columns of light emitting diode segments on the playing field display 22. The strobe inputs to the nine rows of segments are provided over leads 80 through 88 corresponding to rows "0" through "8". The last three strove outputs on leads 86, 87 and 88 are electrically connected directly to the strobe inputs 70, 71 and 72 for the three digit locations 24a–24c of the numeric scoring display 24.

Power to the microprocessor is provided by means of a conventional battery 90, the positive terminal of which is coupled over lead 92 to a first contact 94 of an on-off switch 32, this switch being the switch 32 appearing on the control panel of the game 20. The other terminal 96 of the switch 32 is connected to a positive input voltage terminal of the microprocessor 60, the negative voltage input terminal being connected over lead 98 to the other end of battery 90. A capacitor 100 is connected across the battery 90 to suppress transients during switching conditions.

For emitting game sounds, a speaker 102 is provided and connected to output leads 104 and 106 of the microprocessor 60.

Inputs are provided to the microprocessor 60 by means of the three control switches shown in schematic form in FIG. 6 and designated by the same reference numerals as the control switches 26, 28 and 30 in FIG. 1. These three switches are momentary contact switches with one end thereof connected to ground or to the negative battery lead 98 with the other ends thereof being connected to three input terminals 108–110 of the microprocessor 60.

Figure 7:
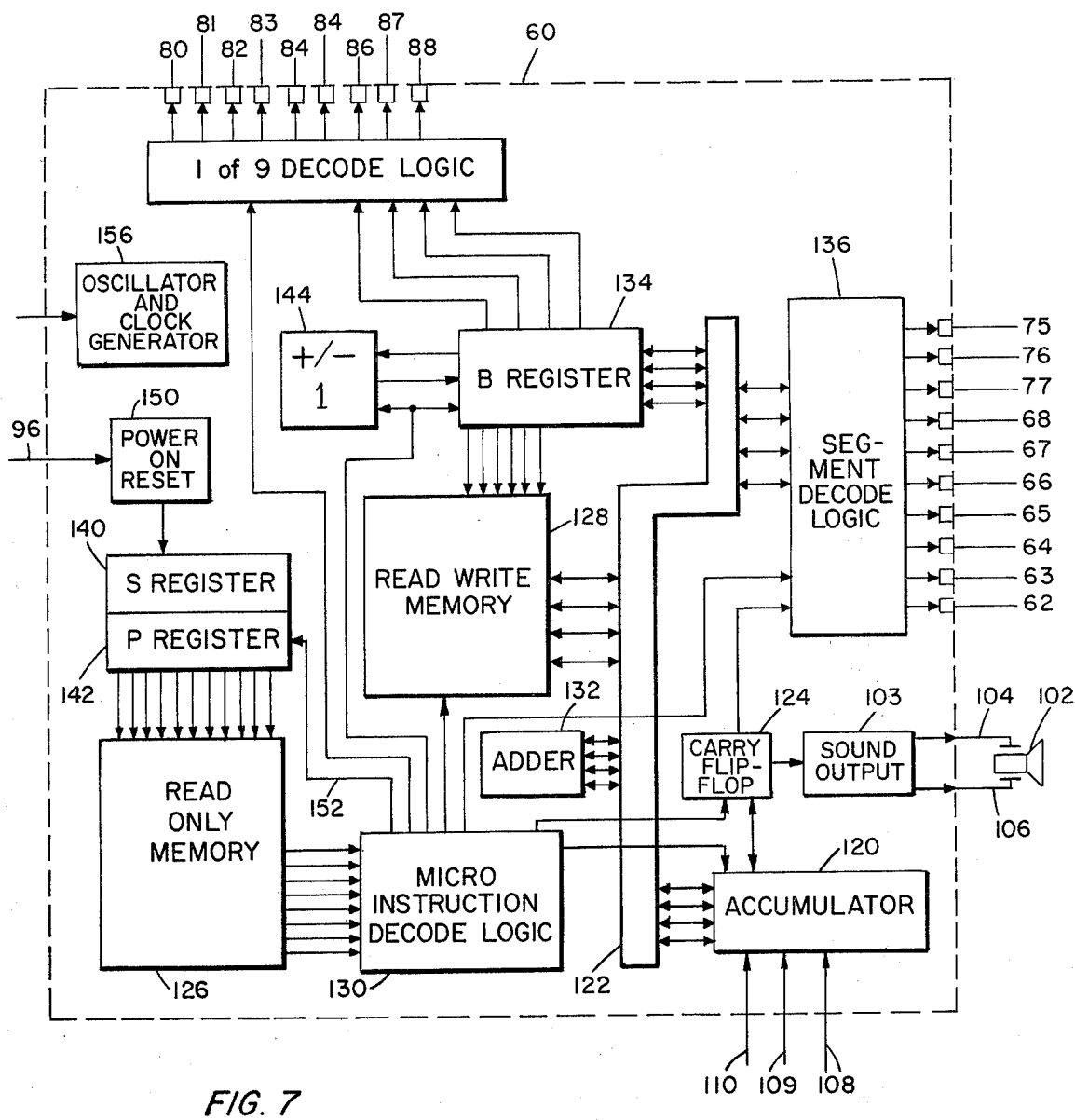
FIG. 7 is a block diagram of the microprocessor used in the diagram of FIG. 6.

Referring now to FIG. 7, the internal architecture of the microprocessor 60 will be discussed. In FIG. 7, for reference purposes, the electrical leads providing the inputs and outputs to the microprocessor have been shown in part and contain reference numerals to enable correlation to the system block diagram of FIG. 6. That is, the segment outputs have been designated 62–68 and 75–77 respectively; the strobe outputs have been designated 80–88 respectively, the speaker 102 outputs are designated by the reference numerals 104 and 106; the positive voltage input has been designated by reference numeral 96 and the three inputs are designed by the leads 108–110. The microprocessor is essentially an accumulator oriented processor, that is input signals from leads 108–110 transfer first into the accumulator 120. The output of accumulator 120 is transferred to a data bus 122, and may under certain events have one digit thereof transferred to a "carry flip flop" 124. Internally, the functional components of the microprocessor 60 include a read only memory 126 a randon access memory 28, microinstruction decode logic 130, an adder 132, a B register 134, segment decode logic 136, strobe decode logic 138, an S register 140, a P register 142, an increment/decrement control logic 144, and system clock 155.

Generally, the microprocessor 60 is a four bit machine with the data transfers being accomplished through four bits of information through the accumulator and onto the data bus 122. Data transfers are effected to the data bus 122 from the adder 132, the RAM or random access memory 128, the B register 134 and the segment decode logic 136.

Upon the initiation of power from lead 96, power is applied through a power control logic 150 into the program register 142, the S register 140 serving as a save register during the execution of certain instructions which require that a prior instruction location be retained pending completion of the existing operations. The program register 142 addresses the read only memory 126 to provide an output to the microinstruction decode logic 130 which then provides a control signal over lead 152 back to the program register 142 for incrementing the program or otherwise instructing the register to save the existing contents as required by the instruction then being executed. The microinstruction decode logic then issues commands and signals as required to the accumulator 120, the carry flipflop 124, the segment decode logic 136, the RAM 128, the strobe decode logic 138, the increment/decrement control logic 144 or the B register 134.

The B register 134 is a RAM address register which is indicated as having six leads therefrom to the RAM 128, the upper two bits of information acting as a pointer to a particular RAM location with the lower four bits providing data for that particular address pointed at.

The RAM address or B register 134 is the primary source of communication with the strobe decode logic which is identified in the block 138 as a "1 of 9" decode logic. That is, only one output of the strobe decode logic 138 goes "high" at any particular interval of time.

The segment decode logic 136, on the other hand, may provide any number of outputs to segment select leads 62–68 and 75–77.

In operation, the microprocessor 60 has the read only memory 126 thereof storing a series of instructions in accordance with predetermined algorithms for all three games. The microinstruction decode logic 130 is hardwired logic for interpreting the instructions from the read only memory 126 and for providing the appropriate controls to the other internal components. The controls to be affected are determined in large part by the inputs provided to the accumulator 120 at the appropriate time intervals over leads 108–110 with the outputs to the speaker 102, to the segment leads 62–68 for controlling the three digit numeric display 24, to the segment leads 75–77 for controlling the playing field display 22, and to the strobe output leads 80–88 for controlling both displays 22 and 24. For each game, upon initialization, the RAM memory 128 has all register locations therein zeroed for receipt of information designating initial assignments for that particular game. The random access memory 128 is essentially a read/write memory used for temporary storage of data or signals during processing. For example, the memory 128 may be configured as a four by twelve configuration, that is four registers, each holding twelve words with the 48 registers selectively addressed by the B register 134. Certain of the registers within the RAM 128 may be assigned particular functions during the course of the game, for example three words at three distinct locations in memory 128 may be assigned the task of keeping track of the "row count" information previously referred to, that is, one word in memory 128 will be continually updated to reflect the current position of a dot, that is an illuminated segment, in a particular column. Other words in particular memory locations of memory 128 will be assigned or dedicated to update certain values associated with the other variables required during the game play. Such other variables may include, for example the score, the speed associated with a particular dot in a given column, timing of a game, and certain "flags".

Figure 8:
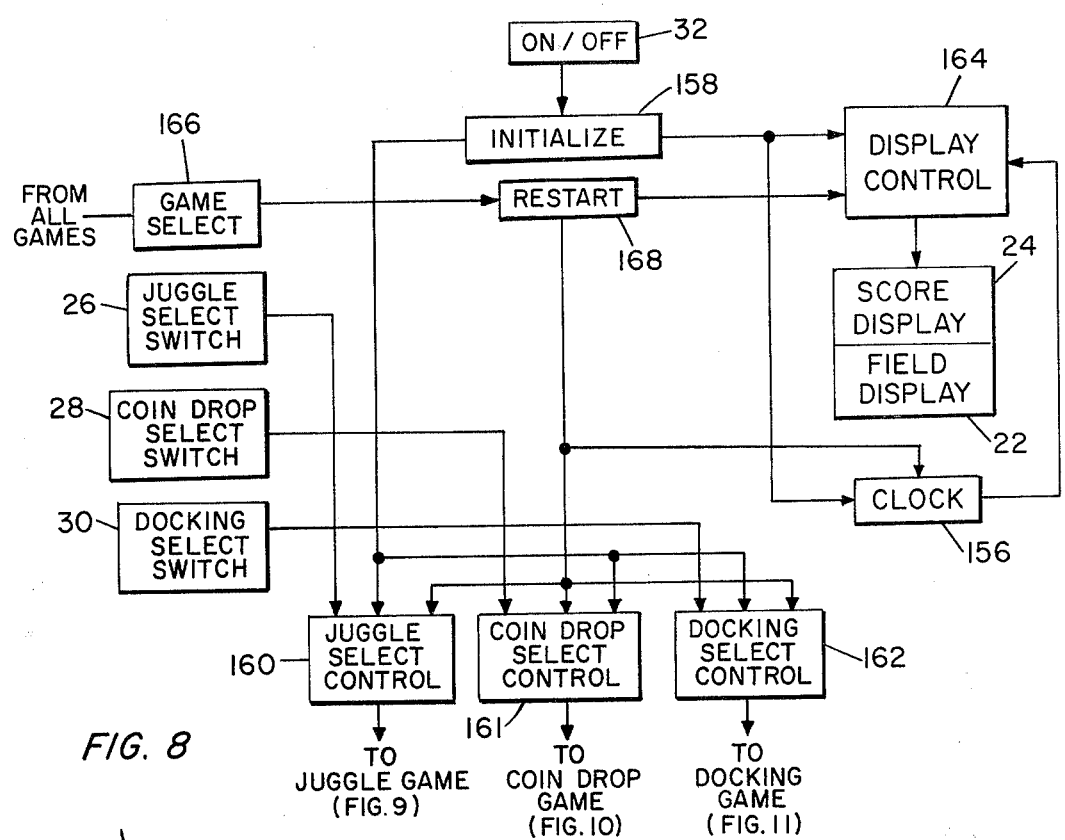
FIG. 8 is a functional block diagram depicting the game control and select functions of the electronics of FIG. 6.
Figure 9:
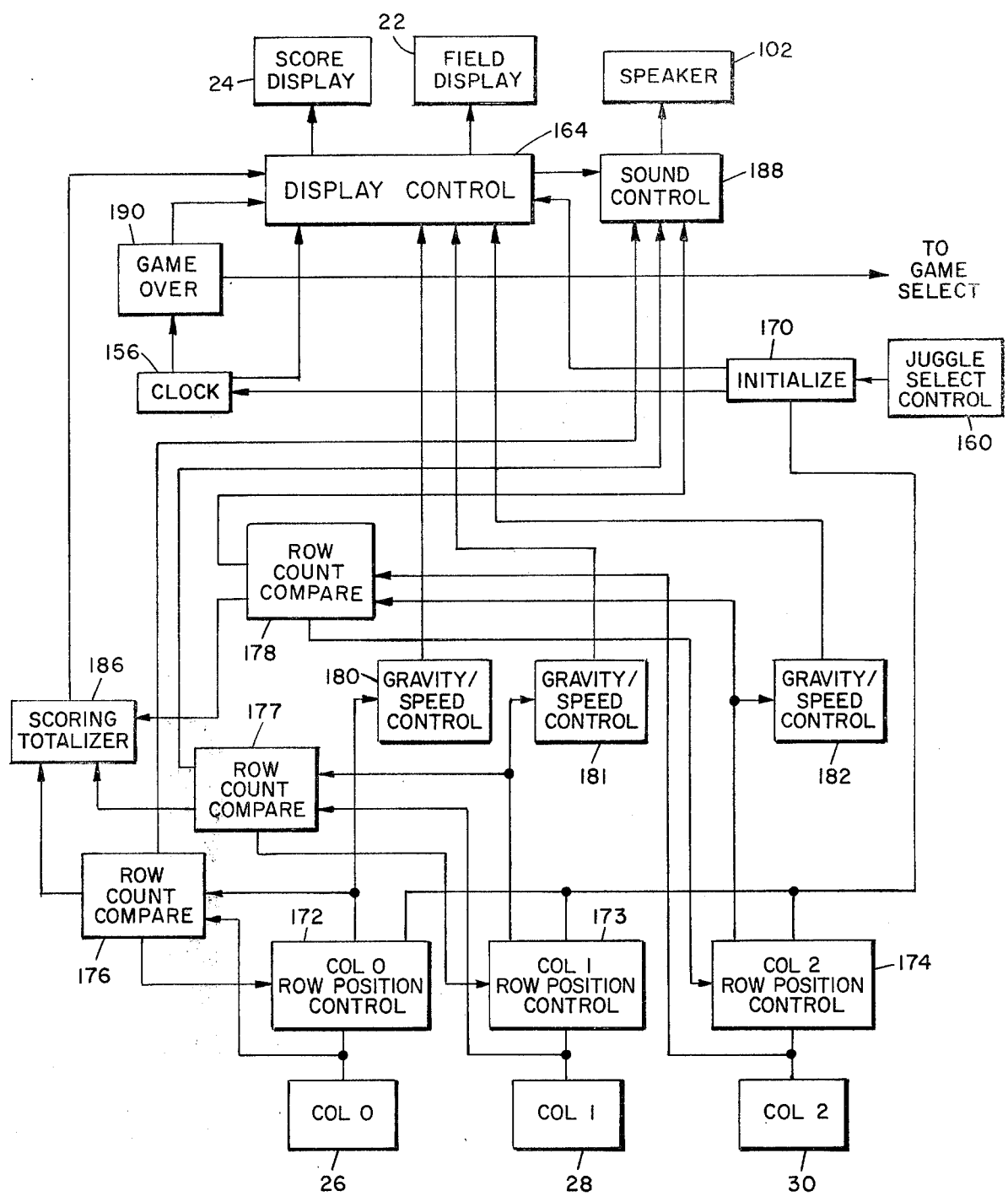
FIG. 9 is a functional block diagram depicting the first game condition.
Figure 10:
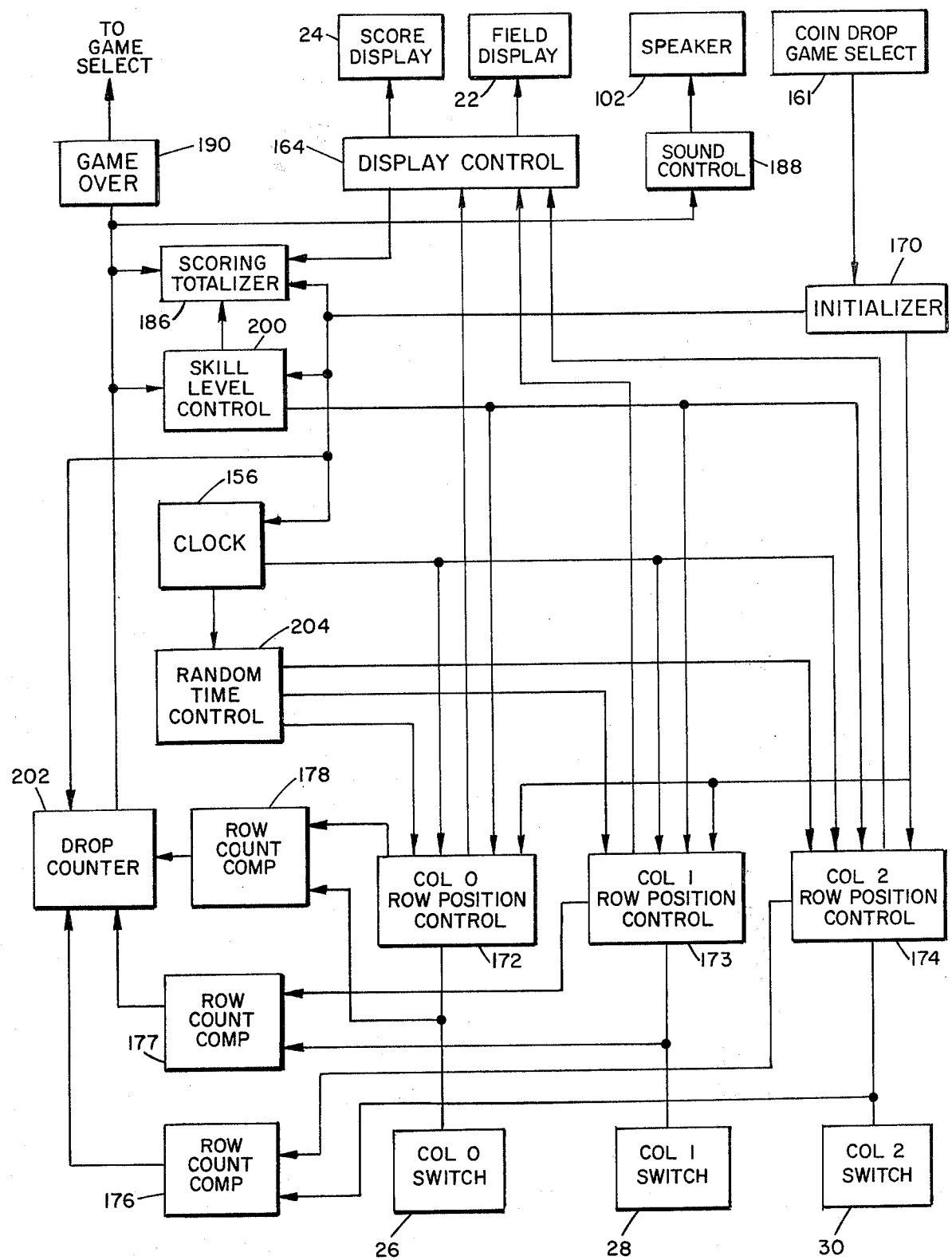
FIG. 10 is a functional block diagram depicting a second configuration.
Figure 11:
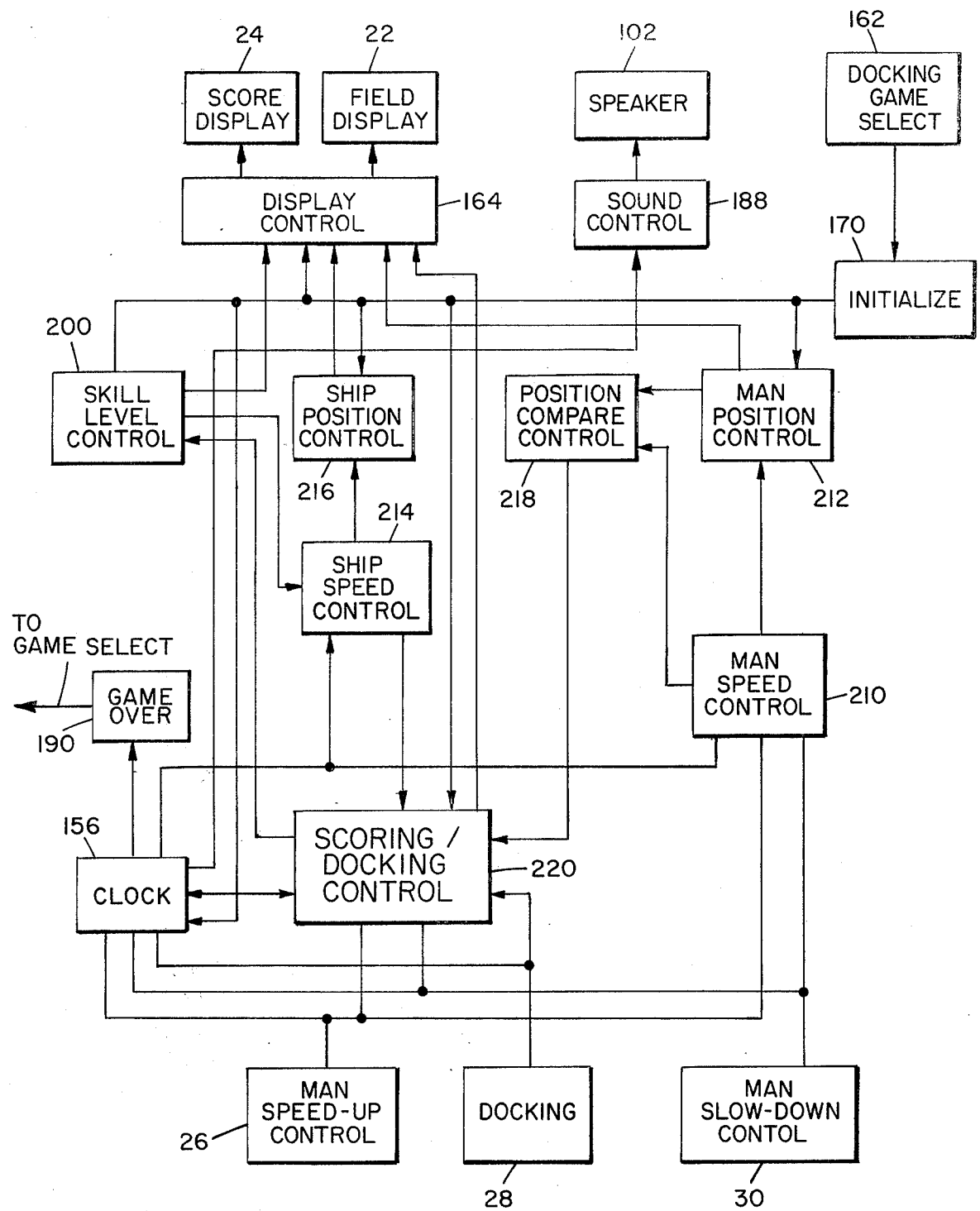
FIG. 11 is a functional block diagram depicting a third game configuration.

The operation of the mciroprocessor 60 will be better understood by reference to the functional block diagrams to be discussed in connection with FIGS. 8 through 11. Briefly, FIG. 8 depicts in block diagram form the game select mode or game control functions performed by the processor 60 while FIGS. 9 through 11 show in block diagram form the juggling game, the coin drop game, and the spaceship/docking game, respectively, these latter three figures depicting the functions performed by the processor 60 in the mode of each game. In all four figures, the rectangular blocks therein corresponding to physical devices in FIGS. 1 through 7 will bear the same reference numerals. For example, as previously discussed the control switches 26, 28 and 30 perform an initial function to select the appropriate game to be played immediately after start up. In FIG. 8, these three switches 26, 28 and 30 are adjacent the rectangles identified as the juggle select switch, the coin drop select switch, and the docking select switch. In FIG. 9, these same three switches can be found adjacent the bottom with reference numerals 26, 28 and 30 with labels in the rectangles for column "0", column "1" and columm "2", these being the control functions assigned when the juggling game is selected to the control switches 26, 28 and 30. That is, these control switches respectively affect the dot illuminated in its respective column. The control switches likewise appear in FIGS. 10 and 11 with different labels within the rectangles depending upon the function assigned for that particular game as will be discussed hereinafter.

Referring particularly to FIG. 8, upon actuation of switch 32 to the "on" position, an initialization signal is generated at block 158 and applied simultaneously to one input of each of the select controllers 160–162. Simultaneously the initialized signal from block 158 goes to the game clock 156 for resetting it to zero while simultaneously initiating the displays 22 and 24 by means of the display controller 164. The display displays three dots in row "0" which then move in sequence to row "8", then down to row "0" where the action repeats itself simulating a row of bouncing balls. Upon initialization after applying power, actuation of one of the control switches 26, 28 or 30 will provide an input signal to one of the select controllers 160–162 respectively for selecting one of three games. Depression of control switch 26 will select the juggling game, while depression or actuation of the control switch 28 will select the coin drop game while actuation of the control switch 30 will select the spaceship/docking game.

The same game sequence selection process will occur after the game 20 has been played and the first game ends, this event being signaled to a game select means 166 which provides for a restart function 168 to again initialize or reset the clock 156, the display controller 164 and the game select controllers 160-162.

Assuming the juggling game has been selected, referring to FIG. 9 the signal from the juggle select controller 160 provides an initialization function 170 to the system clock 156, to the display controller 164 and to the row position controllers 172-174 which essentially control the ball or dot position for each of the columns "0"-"2" respectively depending upon the actuation of the control switches 26, 28 and 30 providing inputs thereto. Upon initialization, in sequence, the display control 164 will clear the score display 24 and field display 22, and shortly thereafter load a number into the row position controllers 172-174, the so-loaded number corresponding to the row in which a dot is to appear on the display field 22 for commencement of game play. For example, a binary number may be loaded into all three row position controllers corresponding to row "0" (that is three dots will appear in row "0" in columns "0", "1" and "2"). The score display 24 at this point will display the numeral "45", this being the time period during which the player has to juggle the balls.

Immediately upon depression of any one of the control switches 26, 28 or 30 the ball in the so-selected column will commence to rise, that is the dot appearing on the display screen as discussed in connection with FIG. 3 will travel upwardly on the display field 22. Functionally, each of the control switches 26, 28 and 30 provides a signal to the row position controllers 172-174 respectively and also to row count comparators 176-178 respectively. Speed control functions are provided as depicted by blocks 180-182 respectively for the three column switches 26, 28 and 30. The output of thr row position controls 172-174 is provided to the gravity/speed controllers 180-182 as well as the row count comparators 176-178. The outputs of the gravity/speed controllers 180-182 are provided to the display controller 164 for selectively and respectively controlling the display field 22 and scoring display 24.

The row count comparison output is provided both to the scoring totalizer 186 as well as back to the row position controllers 172-174. Row count comparison pulses or signals are also provided to a sound controller 188 which ultimately drives the speaker 102 upon the occurrence of certain specified events, such as successful depressions of the control switches 26, 28 or 30 and a ball or dot reaching its highest trajectory. During the game, the system clock 156 continues to count with the count being transmitted to the display controller 164 for decrementing the time remaining on the score display 24. Also, when the clock 156 reaches zero a "game over" signal is transmitted as indicated by block 190 to the display controller 164 to thereby freeze the display while providing a signal to the game select means for restarting the game as discussed in conjunction with FIG. 7.

Functionally, the gravity/speed controls 180-182 affect the speed of successive illumination of the light emitting diode segments in the up as well as down direction during play of the game. The speed of upward or downward movement, that is the rise or fall time is governed by which row was occupied at the time of successful depression of one of the control switches 26, 28 and 30 and the maximum trajectory reached by the ball or dot. The row count information, in accordance with the rules of the game and in accordance with the algorithm programmed into the read only memory 126, in the juggle game causes the following results. The control switches 26, 28 and 30 only have effect when a given ball or dot is moving downwardly and the control button associated with the column is activated when the then illuminated segment is in row "2", "1", or "0". If the depression of one of the control switches coincides with these condition, the row count compare signal from one of the comparators 176-178 increments the scoring totalizer 186 while simultaneously transmitting a signal to the sound controller 188 to audibly indicate the successful event. The control switches 26, 28 and 30 are likewise effective when the ball or dot is "at rest", this being a condition which exists after the ball has gone into a bouncing state as previously discussed with reference to FIG. 3 after a missed catch (depressing the control switch after the dot has reached row "0" and is moving upwardly toward row "2" until resting in row "0") after which the control switch is again effective. Furthermore, depending upon which row is illuminated in a given column at the time of depression of the control switch, the height of trajectory as well as the rise and fall time will likewise change. For example, if coincidence exists between successful depression of control switch 26 with the dot moving downwardly to the dotted line position 40a (row "0") the dot will travel to its highest trajectory as indicated by the solid line 40 in FIG. 3. On the other hand if the dot is moving downwardly and in row "1" when control switch 26 is depressed, the ball or dot will reach the level of row "7"; and similarly, if control switch 26 is depressed when the dot is moving downwardly to the dotted line depiction 40b (row "2") the dot will travel upwardly only to row "6". The rise and fall times determined by the gravity/speed control 180 may be for example approximately two seconds in the first case; approximately one and one-half seconds in the second case and only one second in the third case. This simulation of actual gravity by means of the speed control enhances the play of the game since the player must visually discern the relative position or row of each ball or dot at the time of depression of one of the control switches to maintain the "ball up in the air". Whether or not a particular row position controller 172-174 is effective to alter the position of the display dot is determined by the row count compare information from the comparators 176-178, these controllers also retaining the information as to the direction of travel of the dot to perform its assigned function.

Upon completion of a game of juggle, that is when the clock 156 time runs out, the output of the scoring totalizer is transferred through the display control 164 to the scoring display 24, a game over signal 190 is generated and the display controller 164 maintains the scoring display 24 for a predetermined time period such as three seconds after which an end of game signal is transmitted to restart the games.

Referring now to FIG. 10, there is shown a functional block diagram of the system configuration when the coin drop game is selected by the player. The coin drop game select is initiated at block 160 to initialize at block 170 the row position controllers 172-174, the display controller 164, the scoring totalizer 186, the clock 156, and the skill level control 200. The skill level control 200 is set to the first level which information is provided to the row position controllers 172–174. In this configuration, a drop counter 202 is provided and random time controller 204 is provided. The remaining blocks depict functions similar to or identical with those previously discussed in connection with the juggle game in FIG. 9 with the same functions bearing the same reference numerals.

In the coin drop game upon initialization the row position controls or column "1" and "2" are initially ineffective with the control 172 for column "0" having an initial position to provide a display in that column at row "8". The skill level control 200 is initialized to the first skill level, this corresponding to a coin or dot appearing in row "8", column "0". The control switch 26 is the only effective control at this point. The remaining two switches 28 and 30, while not effective to control the position of the dot or coin in the first column, are effective to increment a round in the event the wrong switch is depressed. The player is allowed a predetermined number of rounds for each game.

As previously discussed, after a random time interval the coin or dot drops in the leftmost column "0", the time duration from the appearance of the dot to the movement of the dot being determined by the random time control 204. As can be seen, there are three outputs from the random time control 204, one to each of the row position controllers 172–174. This output is essentially a one of three select where a pulse appears on one of the leads after a random time interval. The random time controller 204, at the first level, only provides a pulse to the row position controller 172 for the column "0" segments. Similarly, at level two an output signal will appear over one of two leads while at the third level only one of the three leads will have a pulse. Regardless of which level, the pulse will appear at a predetermined random time after the second begins.

Again with respect to the first level skill, if the control switch 26 is depressed when the dot displayed is in row "8" this event will be detected by the row count comparator 176 and the drop counter 202 will be incremented one round. Similarly, if either switch 28 or 30 are depressed at the first skill level this information will be detected by the row count comparators 177 and 178 likewise again incrementing the drop counter 202 signifying completion of a round. If the row count is less than "8" (that is the dot is in a position other than the uppermost row) and the switch 26 is actuated, this coincidence will be detected by the row count comparator 176 which will provide this information to the drop counter 202 indicating a successful catch to provide an output signal to the scoring totalizer 186. If three consecutive successful catches are detected, the skill level controller 200 will be incremented to the next skill level and the random time controller 204 will function to the next skill level, that is, level two. At the second level a coin or dot will appear in "8" of column "0" and column "1" simultaneously. The random time controller 204 will supply a pulse at some random time interval to one or the other of row position controllers 172 and 173, thus initiating the dropping of the coin. Successive segments will be illuminated in the so-selected column. In the event the player presses one of the switches other than the control switch for that column a miss is detected and the drop counter 202 commences to the next round. Similarly, if the column in which the dot drops goes blank signifying that the segment in row "0" has been illuminated and extinguished, and the control switch for that column is then depressed late, a miss is likewise detected. If a control switch 26 or 28 is depressed while the row count is at the highest level (row "8") this will likewise be classified as a miss. Successful depression of the control switch 26 or 28 in the column in which the dot is dropping will result in freezing the display, that is the segment occupied at the time of this coincidence will continue its illumination for a brief period of time afterwards. A successful catch is defined as the row count being greater than or equal to zero but less than eight when the control switch is depressed in that column. Scoring is determined as a function of the skill level and row number for each successful catch, this score being maintained on a running basis in the scoring totalizer 186.

If three consecutive successful catches are not detected at the second skill level prior to a miss, the skill level controller 200 is decremented down to the first level where play commences again. Conversely, if after reaching the second skill level, the player effects three consecutive successful catches, the skill level controller 200 is incremented to the third level at which time the uppermost row in each column is illuminated and the random time controller 204 outputs a pulse to one of the three row position controllers 172–174 to effect the dropping of the coin in the so-selected column. The same rules apply at the third level, that is, depression of the wrong control switch effects a miss, depression of the right control switch with the dot in row "8" will effect a miss, or depression of the right switch with the dot at or above row "0" and below row "8" will effect a catch, each miss or catch concluding a round detected by the drop counter 202. The drop counter 202 will have as part of its function the keeping track of the total number of rounds, the game essentially ending after 25 rounds. The number corresponding to the number of rounds will be part of the initialization process and the counter 202 may either count up or count down as desired until the number of rounds are exhausted at which point the game over control 190 will restart the game. At the conclusion of the number of rounds, the score in the scoring totalizer 186 will be displayed through the display controller 164 on the score display 22 until the next game is selected. In this game, although speed control means are not shown, the dropping of the coin as visually depicted by the moving dots on the playing field display 22 will simulate an object dropping under the force of gravity, that is speeding up as it approaches the lowermost row. Since only one coin is dropping at any point in time, the speed relationship function will remain uniform with this function being incorporated in the row position controllers 172–174. Furthermore, the speed function is simplified since there is no upward direction on the successive illumination to be considered in this game format.

The third of the games which is the spaceship docking game previously described with reference to FIG. 5 will now be discussed with reference to the functional block diagram of FIG. 11. The assignments of the control switches, 26, 28 and 30 are changed by the processor 60 as indicated in the rectangular block for the control switches, these functions being to speed up movement of the dot 50 depicting the man (control switch 26), to slow down the dot 50 depicting the man (control switch 30) and to attempt "docking" (positioning the dot 50 depicting the man in the center of the spaceship pattern of dots 51–54).

Referring now to FIG. 11 also, with reference to FIG. 5 the spaceship/docking game will be described. FIG. 11 shows in functional block diagram form the configuration of the system in the docking game with the control switches 26, 28 and 30 being assigned the functions of speeding up the "man", docking as slowing down the man respectively. The pattern of four dots 51–54 will be referred to as the "ship" and the dot 50 will be referred to as the "man". In the docking game there is a man speed control 210, a man position control 212, a ship speed control 214, a ship position control 216, a position compare control 218 and a scoring-/docking control 220. These functional controls are in addition to the skill level control 200, the clock 156, the game over function 190 as well as the display and sound controls 164 and 188 respectively.

Upon receipt of a docking game select signal 162 the configuration is initialized at 170 to set the initial parameters for commencement of the game. The skill level control 200 is initialized to the first level or round, there being nine possible rounds of twenty seconds each, by way of example. The timer or clock 156 will be set to twenty seconds. The man position control 212 and the ship position control 216 will be set to display the ship position adjacent the lowermost portion of the display 22 and the man position in the centermost column row "8". The scoring/docking control will be initialized to accept data for the various inputs thereto, these inputs being from the three control switches 26, 28 and 30; the clock 156; the position compare control 218; and the ship speed control 214. Movement of the spaceship dots 51–54 is initiated by depression of control switch 30 with movement of the man dot 50 started by subsequent depression of control switch 26.

The position compare control 218 is configured to determine the ship position relative to the man position, and as previously described, for a successful docking the man position or dot 50 must be centered within the pattern of dots 51–54 indicating the ship, with an additional constraint. This additional constraint is that the dot 50, or man, must be moving. Thus, the man speed control 210 must be examined by the position compare control 218 to determine if this constraint is in effect. A "true" signal from the man speed control 210 will indicate that the dot 50 is moving to thereby enable an output from the position compare control 218 to the scoring docking control 220.

After initialization, depression of the control switch 30 will start the ship moving downwardly on the field display 22 and the clock 156 will commence decrementing, the time remaining being displayed on the scoring display 24. The player then controls the speed of the man or dot 50 by manipulating control switches 26 and 30, that is speeding up, or slowing down successive illumination of the dot 50 (always in the center column).

The man position control 212 and the ship position control 216 are constantly being examined by the position compare control 218 and if the man or dot 50 is moving as indicated by a "true" signal from the man speed control 210, a "true" signal is received by the scoring/docking control 220. If at that point, the player depresses docking control switch 28, this coincidence is noted and the display is frozen depicting the dot 50 in the dotted line position 50a in the center of the pattern of dots 51–54 depicting the ship. The successful docking information is transferred through the display control 164 to the field display 22 and to the skill level control 200 to increment the game to the next skill level. At the next skill level or round the ship speed control 214 is incremented to speed up the successive illumination or movement of the pattern of dots 51–54 on the playing field display 22. This speeding up is under control of the clock or timer 156 and during decrementing of the clock 156 the sound control 188 actuates the speaker 102 to provide a series of clicks, proportional to the speed at that skill level.

If a docking is attempted, that is depression of switch 28, when the output of the position compare control 218 is "false", this event will be detected by the scoring docking control 220 which will freeze the display for a short time period to provide the player with a visual indication of the "miss". The timer or clock 156 will stop at the then elapsed time. The player can then restart the round by depressing control switch 30 to restart the clock and initiate the movement of the ship on the field display 22. The player must then depress switch 26 to restart movement of the man position dot 50.

As previously described, the movement of the ship or pattern of dots 51–54 is downwardly on the field display 22 and when the ship reaches the bottom of the display screen it "wraps around" to the top of the display screen and again commences its downward travel.

In the event a round is completed without a successful docking (i.e. 20 seconds has elapsed), the game terminates. The object of the game is to reach the highest level during play of the game, the total play of the game lasting for a maximum of nine rounds of 20 seconds each, or approximately three minutes.

During play of the game, each successful docking is noted by the scoring/docking control 220 which maintains a running total. Upon completion of the nine rounds the scoring total is then displayed via the display control 164 on the scoring display 24. By the rules of the game, scoring is a function of a number of points, such as 100 points, for each successful docking plus 5 points for every second of the clock 156 not used in the last successful round. The clock 156 and the scoring/docking control 220 are in bidirectional communication during play of the game in order to permit stopping of the clock on successful docking, starting of the clock 156 after that event if time is available and for computing the score.

In all three games the game 22 upon initialization and after start illuminates at least one segment in a predetermined column. A start signal then causes segments in that column to be consecutively illuminated, one at a time under control of the processor with the row occupied by the then-illuminated segment being continually monitored. The start signal may be automatic (such as the random time controller 204 for the coin drop game) or initiated by the operator (depression of any switch in the juggle game, or depression of switch 30 with subsequent depression of switch 26 in the docking game to start movement of the ship and man, respectively). Subsequently upon coincidence of depression of the control switch for that column with a predetermined row count, the event is visually ascertained by either reversing the direction of successive illumination of the segments (the juggling game) or freezing the display, i.e., displaying the then illuminated segments (the coin drop game or the docking game).

In accordance with the invention, the game 20 operates in four modes, these being "game select" mode, the "juggling" game mode, the "coin drop" mode, and the "spaceship/docking" mode. In each of these modes the control switches 26, 28 and 30 are assigned functions determined by the mode. Similarly, for each mode the dot pattern displayed is different as determined by the processor 60 in response to the game mode selected.

By reference now to FIG. 12, there is diagramatically illustrated a memory map which indicates the contents assigned to the various registers in the random access memory 128 of the microprocessor 60 (see FIG. 7). In the B6000 microprocessor, the RAM 128 is a scratch pad memory having four registers, each of which has storage for twelve four-bit words, commonly referred to as a 4×12 memory. Essentially there are 48 word locations which may be visualized in a matrix or checkboard such as depicted in FIG. 12, the vertical designations A-D being used for reference purposes to refer to the four registers in the horizontal with the designations A-F across the top of the matrix providing references to the vertical word locations. The B register 134 addresses each of these memory locations as required by the instructions in the read only memory 126. For example, a memory address location of B,A would designate the "CLOCK" memory location. In establishing the modes and games for the system of FIG. 6, the random access memory 128 usually has a preassignment of certain memory locations of the random access memory 128 for functions to be monitored and utilized during play of the game. This pre-assignment of functions to particular memory locations simplifies the instructions required in the read only memory 126 with the type of processor 60 utilized in the game 20. The designations within the memory locations of FIG. 12 are not all-inclusive, only some of the major functions stored in the memory 128 being depicted. Some of the lesser functions, or those functions applicable to only one mode may be stored in certain of the registers or word locations not having functions depicted therein. Such word locations, notwithstanding, may be assigned to retain information pertinent to a particular mode with different information being stored in that word location for a different mode. In such cases, a particular word location or register will have multiple assignments for information storage. Furthermore, as will be discussed hereinafter, even though assigned functions are depicted in the memory map of FIG. 12, depending on the mode the function may vary due to the non-use of that register in the particular selected game mode. The use of the term register hereafter will refer to a word location in FIG. 12.

Registers D,D; D,E; and D,F are assigned the function of maintaining current "row" information, that is the row count information on the then-illuminated dot or segment in a given game. This row count information, by reference to FIG. 6 corresponds to the strobe information or signals outputted from the microprocessor 60 on leads 80–88. As previously discussed in conjunction with FIG. 7 the output of the strobe decode logic 138 activates only one of the strobe output leads at a time, these strobe output leads being energized sufficiently rapidly in conjunction with the segment output leads 75–77 and 62–68 to provide the appearance of a continually illuminated segment or segments.

The registers C,D; C,E; and C,F provide the segment or column information. That is, the information in these three memory locations provide the information for energizing outputs 75–77 from the microprocessor 60 in FIG. 6.

Registers B,D; B,E; and B,F are "status" memory locations. These three memory locations store information during three of the modes on the status of the dots displayed, that is whether the dots are moving up or down; whether the dots are in a bouncing state; and information as to the velocity of movement of the dots. These status conditions are applicable to the game select mode, the juggle game mode, or the coin drop game mode. As will be discussed hereinafter, the memory addresses B,D and B,E have another function for the docking game mode.

Memory registers A,D; A,E; and A,F are timer registers for the dot in each column and are used to increment to the next strobe location or to indicate levels in the game select mode, the juggle mode or the coin drop mode. However, the DOT 1 timer register and DOT 2 timer register have other functions during the docking game.

The register at A,C is indicated as having a dual function, one being to indicate the level or round for the docking game for example and the other function being for the coin drop game to indicate "catches". For the latter function, this register would be incremented for each successful catch and reset after three consecutive successful catches.

Register A,B is used to store the information on the random time interval required for the coin drop game mode and may be used for other functions during the other modes.

Registers or memory locations B,B; C,B and D,B are assigned functions pertaining to the generation of sound for the sound control means 188. The "sound flag" will be set according to the type of sound desired (i.e. a buzz at the end of a game or a beep during the game) or no sound at all. The two sound delay memory locations are accessed as required by the instructions in the read only memory 126 to "toggle" the carry flip flop 124 to provide the pitch and duration of sound output through the speaker 102 at the appropriate game event.

The register D,A is identified as the "mode flag" and will be set with the information according to the particular mode during play of the game.

Registers B,A and C,A are identified as "clock" and "score". In those games in which time is displayed on the scoring display 24 the clock register will provide the information for the display and during those portions of time in which a score other than the time is displayed the score register will provide the information to the score display 24. The score register may be used for example for the score totalizer 186 in all three game modes with the actual display of the corresponding numeric value being determined by other game events.

Any one of the untitled memory locations may be used for certain functional assignments during play of certain games. For example, in the juggle game if a ball is in the bouncing state in a given column as indicated by one of the status registers, the control switch for that column is inhibited until the dot in that column is at rest in row "0". One of the memory registers may be used during this time interval for inhibiting entry into the microprocessor 60 from that control switch. Similarly, other RAM register locations may be assigned to different functions for the storage of information then being processed for that mode.

Since the game rules are different for the spaceship/docking game the functional assignment of certain of the memory locations are used for an additional purpose in this game mode. The rules are different insofar as in the game select mode, the coin drop game mode, and the juggling game mode only one dot is illuminated in a given column. In the docking game mode however, the center column will have two or three dots illuminated (dots 50, 52 and 54 in FIG. 5), there ordinarily being three dots illuminated unless the dot 50 overlies or overlaps one of the dots 52 or 54 at which time the so-overlapped dot will be brighter due to a double strobe being initiated for that segment, one strobe during the ship display cycle and one strobe for the man display cycle.

In this mode there are normally five dots displayed. However, the timer registers and status registers are not used for those functions during the docking game mode. Two each of these registers are used functionally for storing information on the row position of the two additional dots and two of these registers or memory locations are used for man time information and man speed information. These four registers are depicted in FIG. 12 with an asterisk in the lower left corner of those particular memory locations. Specifically register B,D (DOT 2 status) effectively becomes the register for the fourth dot of the spaceship while register B,E (DOT 1 status) becomes the fourth register for column information for that dot. The upper two timer registers provide information regarding the man dot location and speed as well as whether or not the dot 50 representing the man is in a stopped or moving condition to determine whether or not docking occurs.

Thus, with the memory map variables which are repeatedly used and updated during the various modes are stored in preassigned or prearranged convenient locations for the processor 60 to execute the instructions in the read only memory 126 and provide the appropriate segment and strobe information to energize appropriate segments in proper time sequence as well as providing outputs to emit sound. It is to be understood that the game 20 hereinabove described may employ other modes or configurations utilizing a matrix of illuminatable segments to symbolically depict moving objects or indicia under machine control with control switches affecting the display for a predetermined column.

While not believed necessary for a thorough understanding of the present invention, submitted herewith and made a permanent part of the file wrapper of this application is a computer program object code listing. The listing sets forth the binary contents of the listed program memory addresses and may be used directly to program the ROM portion of the microprocessor to simulate the various games hereinabove described. To the extent the Examiner deems such material necessary under the provisions of the Patent Laws, this listing is incorporated herein by reference.

While there has been shown and described a preferred embodiment, it is to be understood that various other adaptations and modifications may be made within the scope of the invention.

What is claimed is:

1. In an electronic game, the combination comprising:
   display means having illuminatable segments configured in an array of a plurality of rows and a plurality of columns;
   means for selectively illuminating at least one segment in a predetermined column;
   means for successively illuminating, one at a time, segments in said predetermined column commencing with the segment adjacent said at least one segment;
   means for monitoring the row occupied by the then-illuminated segment;
   a plurality of manually operable switches equal in number to the number of columns, each of said switches being positioned adjacent to, and in alignment with, one of said columns; and
   means responsive to said monitoring means and manual operation of the one of said switches adjacent said predetermined column for interrupting the sequence of illumination to cause one of (a) reversing the direction of successive illumination and (b) stopping the successive illumination and displaying the then-illuminated segment.

2. The combination according to claim 1 wherein one of said switches initiates the successive illumination of the segments in said predetermined column.

3. The combination according to claim 1 wherein said game further includes game select means for selecting one of the plurality of games, and means responsive to said game select means for altering the functional assignment for each of said switches in accordance with the rules of the so-selected game.

4. The combination according to claim 1 wherein said means for successively illuminating said segments is responsive to operation of the one of said switches adjacent said predetermined column, and said means responsive to manual operation is responsive to a subsequent depression of the one of said switches adjacent said predetermined column and responsive to said monitoring means for reversing the direction of successive illumination of said segments only if the so-illuminated segment is in a predetermined row.

5. The combination according to claim 1 wherein said game further includes random time means, said means for successively illuminating are in response to said random time means, and said means responsive to manual operation is responsive to operation of the one of said switches adjacent said predetermined column and to said monitoring means for stopping the successive illumination only if the so-illuminated segment is in a predetermined row.

6. The combination according to claim 1 wherein said means for successively illuminating illuminates one segment in a predetermined column and also illuminates a pattern of segments in a plurality of columns and said means for successively illuminating segments successively illuminates the said one segment as well as the pattern of segments in maintained relation.

7. The combination according to claim 6 wherein said means responsive to manual operation of the one of said switches and said monitoring means stops the successive illumination and displays the then-illuminated pattern of segments and the then-illuminated said one segment only if said one segment is in a given relation to said pattern of segments.

8. In an electronic game, the combination comprising:
   display means having illuminatable segments configured in an array of a plurality of rows and a plurality of columns;
   a plurality of manually operable switches equal in number to the number of columns, each of said switches being positioned adjacent to, and in alignment with one of said columns;
   processor means for receiving input signals in response to manual operation of said switches and for providing output signals to said display means;

means within said processor means for providing a game select mode for illuminating a predetermined sequence of said segments indicative of said mode;

means within said processor means for providing at least one game mode in response to actuation of at least one of said switches;

means within said processor means responsive to selection of said at least one game mode for selectively illuminating at least one segment in a predetermined column;

means within said processor means operative in said at least one game mode for:

(a) assigning control functions to the input signals in accordance with the rules of the selected game;

(b) illuminating at least one segment in a predetermined column;

(c) sequentially illuminating, one at a time, the segments in said predetermined column starting with the segment adjacent said at least one segment, in response to one of (i) lapse of a time interval and (ii) actuation of the switch adjacent said predetermined column; and (d) interrupting the sequential illumination of said segments in response to actuation of the switch adjacent said column.

9. The combination according to claim 8 wherein said means within said processor means operative in said at least one game mode further includes means for monitoring the row of the then-illuminated segment in said predetermined column and for interrupting the sequential illumination in response to actuation of the switch adjacent said column only if the then-illuminated segment is in a predetermined row.

10. The combination according to claim 9 wherein said means within said processor means operative in said at least one game mode illuminates one segment in each column, actuation of the switch adjacent a column commences sequential illumination of the segments in said column, and subsequent actuation of the switch adjacent said column reverses the direction of sequential illumination of the segments in that column only if the then-illuminated segment is in a predetermined number of rows whereby to simulate a juggling game.

11. The combination according to claim 10 wherein said means within said processor means operative in said at least one game mode includes means for varying the rate of successive illumination of said segments in said predetermined column for simulating the effect of gravity.

12. The combination according to claim 8 wherein said means within said processor means operative in said at least one game mode further includes means for generating a random time interval, and the segment illuminted in said predetermined column is in the row remotest from the swtich adjacent said predetermined column and the sequential illumination commences in response to lapse of a time interval determined by said means for generating a random time interval.

13. The combination according to claim 12 wherein said means within said processor means operative in said at least one game mode interrupts the sequential illumination to display the then-illuminated segment in response to actuation of the switch adjacent said predetermined column for simulating a falling object and a catch type game.

14. The combination according to claim 13 wherein said means within said processor means operative in said at least one game mode further include means for increasing the rate of sequential illumination of the segments in said predetermined column as the row of the then-illuminated segment approaches nearer to the switch adjacent said column.

15. The combination according to claim 14 wherein said means within said processor means operative in said at least one game mode further includes means for counting the number of successful actuations of the switch adjacent said column and said game further includes a scoring display means for providing a visual indication proportional to the output of said counting means.

16. The combination according to claim 15 wherein said means within said processor means operative in said at least one game mode further includes skill level means responsive to the output of said counting means for increasing the number of columns having at least one segment illuminated therein and said random time interval means commences successive illumination of the segments in only one of said columns.

17. The combination according to claim 16 wherein said display means includes three columns, said means within said processor means operative in said at least one game mode includes means for illuminating the segment in a first column remotest from the switch adjacent said column, and said skill level means illuminates an additional segment in the adjacent row only if said counting means counts a predetermined number of consecutive successful acutations of the switches.

18. The combination according to claim 8 wherein said display means includes at least three columns and said means within said processor means operative in said at least one game mode illuminates a predetermined pattern of segments in said at least three columns and at least one other segment in a predetermined column for simulating a spaceship and a man in space.

19. The combination according to claim 18 wherein said means within said processor means operative in said at least one game mode causes sequential illuination of the segments for maintaining the visual appearance of said pattern in response to actuation of the switch adjacent one of the columns having a segment of said predetermined pattern of segments illuminated.

20. The combination according to claim 18 wherein said means within said processor means operative in said at least one game mode causes sequential illumination of the segments in said predetermined column starting with the segment adjacent said at least one other segment and the switch adjacent the column in which said at least one other segment is illuminated interrupts the sequential illumination of said predetermined pattern of segments and said at least one other segment for displaying the then-illuminated segments upon actuation of said switch.

21. The combination according to claim 20 wherein said means within said processor means operative in said at least one game mode includes scoring means operable in response to stopping the sequence of illumination with said at least one other segment being illuminated in a predetermined row relative to the row of the then-illuminated pattern of segments.

22. The combination according to claim 21 wherein said display means includes three columns, and said means within said processor means operative in said at least one game mode illuminates said at least one other segment in the center column and at least one segment in each of the columns for said pattern of segments.

23. In an electronic game, the combination comprising:
- display means having illuminatable segments configured in an array of three columns and a plurality of rows;
- three manually operable switch means, each of said switches being positioned adjacent one of said columns;
- processor means for receiving input signals from said switch means and for providing output signals to said display means for selectively illuminating the segments of said display means;
- means within said processor means for providing a plurality of modes of operation of said game and for assigning control functions to the input signals of said switch means in accordance with the mode for providing a different sequence of illumination of said segments of said display means in accordance with the mode and for providing a different effect on the sequence of illumination in accordance with the control function assigned to the inputs of each of the switches.

24. The combination according to claim 23 wherein said processor means further includes scoring means and said game further includes a scoring display means for providing a visual depiction of said scoring means.

25. The combination according to claim 23 wherein said game includes a game select mode and three game modes and said processor means in said game select mode enables selection of one of said game modes in response to actuation of one of said switch means.

* * * * *